United States Patent [19]

Morikawa et al.

[11] 4,020,118

[45] Apr. 26, 1977

[54] PROCESS FOR PRODUCING ISOPRENE TRIMERS

[75] Inventors: Hiroyuki Morikawa; Takahiro Sato; Isao Okada, all of Ibaraki, Japan

[73] Assignee: Mitsubishi Petrochemical Company Limited, Japan

[22] Filed: Feb. 11, 1976

[21] Appl. No.: 657,308

[30] Foreign Application Priority Data

Feb. 17, 1975 Japan .............................. 50-19591

[52] U.S. Cl. .......................... 260/666 B; 260/666 A
[51] Int. Cl.$^2$ .................. C07C 3/035; C07C 13/27
[58] Field of Search ..................... 260/666 B, 666 A

[56] References Cited

UNITED STATES PATENTS

| | | | |
|---|---|---|---|
| 2,972,640 | 2/1961 | Burks et al. | 260/666 B |
| 3,152,158 | 10/1964 | Clark | 260/666 B |
| 3,250,817 | 5/1966 | Lapporte | 260/666 B |
| 3,251,893 | 5/1966 | Feldman et al. | 260/666 B |
| 3,346,608 | 10/1967 | Kutepow et al. | 260/666 B |
| 3,364,273 | 1/1968 | Clark et al. | 260/666 B |
| 3,522,321 | 7/1970 | De Young | 260/666 B |
| 3,641,175 | 2/1972 | Wilke et al. | 260/666 B |
| 3,920,762 | 11/1975 | Wilke et al. | 260/666 B |
| 3,929,922 | 12/1975 | Wilke et al. | 260/666 B |

*Primary Examiner*—Veronica O'Keefe
*Attorney, Agent, or Firm*—Robert E. Burns; Emmanuel J. Lobato; Bruce L. Adams

[57] ABSTRACT

A process for producing isoprene trimers by the catalytic oligomerization of isoprene which comprises effecting said oligomerization in the presence of a catalyst system comprising:
 A. a reducible nickel compound;
 B. an aluminum compound of the formula:

$$AlR_m(OR')_{3-m}$$

wherein R and R' respectively represent an alkyl group having from 1 to 10 carbon atoms or an aryl group, and m is an integer of 0 to 3;
 C. a reaction product of triethyl phosphite and pentaerythritol; and
 D. a monohydric alcohol having from 2 to 6 carbon atoms.

14 Claims, No Drawings

PROCESS FOR PRODUCING ISOPRENE TRIMERS

BACKGROUND OF THE INVENTION

The present invention relates to a process for producing isoprene trimers through the use of catalysts having improved activity with improved selectivity to cyclic trimers.

Heretofore, for preparing oligomers of an 1,3-diolefin, a process for polymerizing 1,3-diolefins in the presence of a catalyst prepared by mixing an acetylacetonato compound of iron, cobalt or nickel with an organometallic compound of a metal selected from Groups I, II and III of the periodic table in the presence of an electron donor (e.g., Japanese Pat. No. 16882/63) has been known. Also known is a process for polymerizing an 1,3-diolefin in the presence of catalyst systems comprising a nickel complex such as nickel acetylacetonate, a reducing agent such as lithium boron hydride and a limited phosphite such as triphenyl phosphite (Zakharkin. Izuest. Akad, Nauk. S.S.S.R. 1964, 168). Furthermore, U.S. Pat. No. 2,972,640 discloses a process for producing dimethyl cyclooctadiene, which is a cyclic dimer of isoprene, as a main product by using a catalyst consisting of a complex of nickel carbonyl and triphenyl phosphite.

Recently, a process for producing a cyclic trimer of isoprene in which a catalyst comprising a combination of bisoctadiene nickel, a reducing agent and a particular phosphite in used (Japanese Pat. Nos. 56950/74 and 56951/74) has been proposed.

However, according to our belief, the prior methods referred to above may be further improved in the conversion of isoprene, concentration of catalyst used, or the selectivity to trimers.

SUMMARY OF THE INVENTION

It has now been formed that an improvement in selectivity to a cyclic trimer and reduction in by-products having boiling points higher than that of the trimer can be attained in the oligomerization of isoprene when a catalyst system comprising (A) a reducible nickel compound, (B) an aluminum compound and (C) a phosphorus compound which is a reaction product of triethyl phosphite and polyhydric alcohol in combination with (D) a lower monohydric alcohol which serves to enhance the performance of the specified phosphorus compound is used.

Therefore, in accordance with the present invention, there is provided a process for producing an isoprene trimer by the catalytic oligomerization of isoprene which comprises effecting said oligomerization in the presence of a catalyst system comprising:

A. a reducible nickel compound:
B. an aluminum compound of the formula:

wherein R and R' respectively represent an alkyl group having from 1 to 10 carbon atoms or an aryl group, and $m$ is an integer of 0 to 3;

C. a reaction product of triethyl phosphite and pentaerythritol; and

D. a monohydric alcohol having from 2 to 6 carbon atoms.

The present invention provides a catalyst having improved activity with improved selectivity to a cyclic trimer.

DETAILED DESCRIPTION

1. CATALYST

A. Reducible nickel compound

The term "a reducible nickel compound" used herein refers to a nickel compound which can be easily reduced by an alkylmetal compound, especially by an alkyl aluminum compound. Examples of the reducible nickel compound are: (1) olefin-nickel complexes such as biscyclo $C_5 - C_8$ alkadiene nickel e.g. biscyclopentadiene nickel and bis-cyclooctadiene nickel; bis-vinyl cyanide nickel, e.g. bis-acrylonitrile nickel, and bis-formylivinyl nickel, e.g. bisacrolein nickel; (2) nickel (II) salts of $C_1$ to $C_{20}$ monocarboxylic organic acid such as nickel octanoate, nickel naphthenate, nickel caprate, nickel stearate, nickel formate, nickel benzoate and nickel octenate; and (3) nickel (II) chelate salts such as bis-acetylacetonatonickel (II), nickel (II) acetylacetate, bis-salicyaldehyde nickel (II), bis-ortho-hydroxyacetophenone nickel (II) and nickel (II) dibenzoin methane. Among these nickel compounds, biscyclooctadiene nickel, nickel naphthenate, nickel stearate, bis-acetylacetonatonickel (II) and nickel (II) acetylacetate are particularly preferred.

B. aluminum compound

The aluminum compound usable for the process of the present invention has the following formula:

wherein R and R' respectively represent an alkyl group having from 1 to 10 carbon atoms or an aryl group such as phenyl or tolyl, and $m$ is an integer of 0 to 3.

Examples of the aluminum compound are: trimethylaluminum, triethylaluminum, tripropylaluminum, triisobutylaluminum, ethoxydiethylaluminum, ethoxydiisobutylaluminum, triphenylaluminum, trinormalhexylaluminum, phenoxydiethylaluminum, triocytaluminum and tridecyl aluminum. Among these aluminum compounds, triethyl aluminum, triisobutyl aluminum, ethoxydiethyl aluminum, trioctyl aluminum, tridecyl aluminum and phenoxydiethyl aluminum are particularly preferred.

C. reaction product of triethyl phosphite and pentaerythritol.

This reaction product can be, for example, prepared by using the method described in *Inorganic Chemistry*, Vol. 1. No. 2 May 1962. p. 392 (by C. W. Heitsch and J. G. Vorkade). Thus, a mixture of triethyl phosphite and pentaerylthritol in a molar ratio of triethyl phosphite to pentaerythritol of 0.5 to 1.5 is heated under reflux at a temperature of 75° to 150° C for 2 to 3 hours. The reaction product thus obtained can be used as it is without isolation.

The reaction product is considered to be a mixture of a mono-substituted product, a di-substituted product and a tri-substituted product, the di- and tri- substituted products being useful. However, the presence of the mono-substituted compounds has no detrimental effect.

D. monohydric alcohol having from 2 to 6 carbon atoms

The alcohols usable for the present invention are straight or normal, branched chain or cyclic saturated monohydric alkanols having from 2 to 6 carbon atoms. Examples of such alcohols are ethanol, n-propanol, isopropanol, n-, sec-, and tert- butanols, n-, sec-, and tert-amyl alcohols, hexyl alcohols such as n-hexyl alcohol and cyclohexyl alcohol. Normal $C_2 - C_6$ alkanols are representative.

2. CATALYST COMPOSITION

The proportions of the ingredients used in the catalyst system of the present invention are critical, and, preferably, have the following ranges.

If the quantitative balance of the ingredients is destroyed, the catalytic performance of the resulting catalyst tends to be lowered.

A. reducible nickel compound (Ni)

The quantity of the reducible nickel compound Ni to isoprene (IP) to be oligomerized, that is, the mole ratio of (Ni)/(IP), is in the range of 0.0005 to 0.1, preferably 0.0001 to 0.05.

B. aluminum compound (Al)

The quantity of the aluminum compound (Al) may vary depending upon the quantity of the monohydric alcohol (D) used. Usually, the mole ratio of (Al)/(Ni) is in the range of 1 to 20, preferably 2 to 10.

C. reaction product of triethyl phosphite and pentaerythritol

The reaction product is used in a mole ratio of 0.05 to 4, preferably 0.1 to 2, based on the nickel compound.

D. monohydric alcohol having from 2 to 6 carbon atoms

For ensuring that the phosphorus compound (C) will exhibit its performance more effectively and the formation of by-products having a higher boiling point than that of an isoprene trimer will be effectively suppressed, the quantity of the alcohol is critical. If the alcohol is particularly used in large amounts, it may have adverse effects on the aluminum compound. The alcohol is used in a mole ratio of 0.1 to 2, preferably 0.2 to 1.5, based on the aluminum compound.

3. METHOD OF PREPARING THE CATALYST

The present catalyst may be prepared by mixing in an inert gas the respective ingredients (A), (B), (C) and (D) together at one time or in steps. In this preparation stage, isoprene monomer can be caused to be present.

The active catalyst is prepared, preferably at 0° to 80° C, by adding under stirring the reaction product (C) of triphosphite and pentaerythritol in the monohydric alcohol (D) to the reducble nickel compound (A) in solution, and, adding the aluminum compound (B) to the resultant mixture.

In this case, a catechol or a quinoline may be added in order to suppress the formation of by-products of higher boiling points, if desired.

The solvent which may be used in the catalyst preparation is preferably that to be used in the subsequent trimerization process.

4. CATALYTIC TRIMERIZATION

The solvent which may be used in the catalytic trimerization of isoprene is an inert solvent which is inactive to the catalyst system. Examples of the solvent are aromatic hydrocarbons such as benzene, toluene and xylenes and aliphatic hydrocarbons such as hexanes and heptanes. The solvent may be used alone or in mixtures of two or more selected from the above-mentioned solvents. Aromatic hydrocarbons having good solubilizing capability for the catalyst are particularly preferred.

The reaction temperature is in the range of 60° to 200° C, preferably 80° to 150° C.

The reaction pressure may be atmospheric or superatmospheric, a pressure not greater than 10 atmospheres being preferable in view of economy of the reaction apparatus.

In order that those skilled in the art may better understand how the present invention may be practiced, the following examples are given by way of illustration and not by way of limitation.

EXAMPLES 1 THROUGH 6

In a 500 ml autoclave the inner atmosphere of which was previously replaced by argon gas, were mixed at 40° C, in each Example, the solvents, nickel compound, aluminum compound, reaction product of triethyl phosphite and pentaerythritol (tri-substituted product) and monohydric alcohol indicated in type and in quantity in Table 1 to prepare a catalyst.

The reaction product of triethyl phosphite and pentaerythritol was prepared as follows: 5 to 6 drops of triethylamine were added to an equimolar mixture of triethyl phosphite and pentaerythritol. Refluxing of the resulting mixture started at a temperature of 75° C. The mixture was heated to a temperature of 130° C under stirring for 3 hours while the liberated ethanol was distilled off. At the end of that time, the desired reaction product was obtained.

68 g of isoprene was added to the catalyst and the mixture was agitated at a temperature of 100° C for 6 hours in the case of Examples 1, 2 and 4 and at a temperature of 120° C for 5 hours in the case of Examples 3, 5 and 6, respectively. Methanol was then added to the reaction mixture to kill the catalyst and the resultant mixture was distilled to isolate the product.

The distillation was carried out under a reduced pressure of 2mm Hg to produce an isoprene trimer distillate boiling at 90° to 110° C. The distillate was subjected to a gas chromatography and an ozone decomposition method to determine its structural isomer composition. The results are shown in Table 1. In Table 1, TMCDT (trimethyl cyclododecatriene) has the following formula:

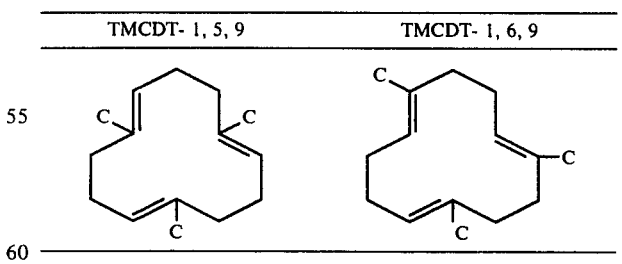

TMCDT- 1, 5, 9      TMCDT- 1, 6, 9

Table 1

| Ex. No. | Solvent*[1] (ml) | (A)*[2] (g) | (B)*[2] (g) | (C)*[2] (g) | (D)*[2] (g) | Conversion of isoprene (%) | Selectivity to trimer (%) | L/C*[3] | 1,5,9/1,6,9*[4] |
|---|---|---|---|---|---|---|---|---|---|
| 1 | T 100 | nickel acetylacetonate | triethyl aluminum | 0.82 | n-butyl alcohol | 89 | 45 | 5/95 | 50/50 |

Table 1-continued

| Ex. No. | Solvent*1 (ml) | (A)*2 (g) | (B)*2 (g) | (C)*2 (g) | (D)*2 (g) | Conversion of isoprene (%) | Selectivity to trimer (%) | L/C*3 | 1,5,9/1,6,9*4 |
|---|---|---|---|---|---|---|---|---|---|
| 2 | T 100 | biscycloocta-dierenickel 1.29 5.50 | ethoxy diethyl aluminum 1.14 10.4 | 4.92 | n-amyl alcohol 0.74 7.04 | 90 | 41 | 5/95 | 49/51 |
| 3 | T 100 | nickel acetyl-acetonato 1.54 | triethyl aluminum 2.05 | 1.23 | n-butyl alcohol 1.33 | 82 | 43 | 4/96 | 50/50 |
| 4 | B 100 | nickel naphtenate 2.55 | triethyl aluminum 2.74 | 0.49 | isopropyl alcohol 0.72 | 80 | 42 | 7/93 | 48/52 |
| 5 | B 100 | nickel acetyl-acetonate 2.57 | triisobutyl aluminum 9.90 | 3.28 | n-butyl alcohol 3.70 | 86 | 44 | 4/96 | 51/49 |
| 6 | X 100 | nickel naphtenate 4.25 | triisobutyl aluminum 3.96 | 1.64 | n-amyl alcohol 1.76 | 85 | 42 | 7/93 | 45/55 |
| 7 | T 100 | nickel acetyl-acetonato 5.14 | trioctyl aluminum 13.50 | 1.64 | n-hexyl alcohol 4.10 | 84 | 43 | 6/94 | 52/48 |
| 8 | T 100 | nickel acetyl-acetonato 2.57 | tridecyl aluminum 9.02 | 1.64 | ethanol 0.92 | 81 | 44 | 5/95 | 49/51 |
| 9 | B 100 | nickel naphtenate 4.25 | phenoxy diethyl aluminum 6.26 | 3.28 | n-hexyl alcohol 1.00 | 83 | 40 | 4/96 | 50/50 |

Note
*1B : benzene T : toluene X : xylene
*2(A) : reducible nickel compound (B) : aluminum compound (C) : reaction product of triethyl phosphite and pentaerythritol (D) : monohydric alcohol
*3ratio of a linear trimer/a cyclic trimer in the trimer obtained.
*4ratio of TMCDT-1,5,9/TMCDT-1,6,9 in the TMCDT obtained.

COMPARATIVE EXAMPLES 1 THROUGH 2

In Comparative Example 1, an isoprene trimer was prepared according to the procedure described in Example 1 except that the reaction product of triethyl phosphite and pentaerythritol and n-butyl alcohol were not used.

In Comparative Example 2, an isoprene trimer was prepared according to the procedure described in Example 1 except that n-butylalcohol was not used and triethyl phosphite only was used.

The results are shown in Table 2 together with the results of Example 1.

Table 2

| | Conversion of isoprene % | Selectivity to trimer % | Selectivity to higher boiling products % | L/C |
|---|---|---|---|---|
| Example 1 | 89 | 45 | 20 | 5/95 |
| Comparative Example 1 | 65 | 16 | 60 | 31/69 |
| Comparative Example 2 | 56 | 18 | 19 | 20/80 |

It is apparent from Table 2 that when the catalyst system containing no reaction product of triethyl phosphite and pentaerythritol and butanol is used, selectively to trimer is reduced, and the content of cyclic trimer in the trimer is remarkably reduced, while higher boiling by-products including polymers are increased.

Further, the catalyst system containing triethyl phosphite alone and no butanol results in decreased selectivity to trimer (increased dimer by-product) and decreased content of cyclic trimer in the trimer product.

We claim:

1. In a process for producing a cyclic trimer of isoprene by oligomerization of isoprene over a catalyst, the improvement which comprises contacting isoprene a catalyst consisting essentially of:
   A. a reducible nickel compound;
   B. an aluminum compound of the formula:

$AlR_m(OR')_{3-m}$ wherein R and R' respectively represent an alkyl group having from 1 to 10 carbon atoms or an aryl group, and m is an integer of 0 to 3;
   C. a reaction product of triethyl phosphite and pentaerythritol; and
   D. a monohydric alcohol having from 2 to 6 carbon atoms.

2. The process as claimed in claim 1 in which the reducible nickel compound is selected from the group consisting of olefin-nickel complexes, nickel (II) salts of a $C_1 - C_{20}$ monocarboxylic acid, and nickel (II) chelate salts.

3. The process as claimed in claim 2 in which the reducible nickel compound is selected from the group consisting of bis-cyclo $C_5 - C_8$ alkadiene nickels, bis-vinyl cyanide nickels, and bis-formylvinyl nickels.

4. The process as claimed in claim 3 in which the bis-cyclo $C_5 - C_8$ alkadiene nickel is selected from bis-cyclopentadiene nickel and bis-cyclooctadiene nickel.

5. The process as claimed in claim 3 in which the vinyl cyanide nickel is bis-acrylonitrile nickel.

6. The process as claimed in claim 3 in which the bis-formylvinyl nickel is bis-acrolein nickel.

7. The process as claimed in claim 2 in which the nickel (II) salt of a $C_1 - C_{20}$ monocarboxylic acid is selected from nickel (II) formate, nickel (II) octanoate, nickel (II) caprate, nickel (II) stearate, nickel (II) octenate, nickel (II) naphthenate, and nickel (II) benzoate.

8. The process as claimed in claim 2 the nickel (II) chelate salt is selected from bis-acetylacetonatonickel (II), nickel (II) acetylacetate, bis-salicylaldehyde nickel (II), bis-ortho-hydroxyacetonphenone nickel (II), nickel (II) dibenzoin methane.

9. The process as claimed in claim 1 in which the aluminum compound is selected from the group consisting of triethylaluminum, triisobutylaluminum, ethoxydiethylaluminum, trioctylaluminum, tridecylaluminum and phenoxy-diethylaluminum.

10. The process as claimed in claim 1 in which the reaction product of triethyl phosphite and pentaerythritol is a reaction product of triethyl phosphite and pentaerythritol in a molar ratio of 0.5 to 1.5 at a reaction temperature of 75° to 150° C under reflux for 2 to 3 hours.

11. The process as claimed in claim 1 in which the monohydric alcohol is a normal alkanol of 2 to 6 carbon atoms.

12. The process as claimed in claim 1 in which the catalyst is prepared at 0° to 80° C by adding the reaction product (C) of triethyl phosphite and pentaerythritol in the monohydric alcohol (D) to the reducible nickel compound (A) in solution, and adding the aluminum compound (B) to the mixture thus produced.

13. The process as claimed in claim 2 in which the molar ratio of the catalyst ingredients is:

| (A)/isoprene | 0.0005 to 0.1 |
| (B)/(A) | 1 to 20 |
| (C)/(A) | 0.05 to 4 |
| (D)/(B) | 0.1 to 2 |

14. The process as claimed in claim 1 in the molar ratio is:

| (A)/isoprene | 0.001 to 0.05 |
| (B)/(A) | 2 to 10 |
| (C)/(A) | 0.1 to 2 |
| (D)/(B) | 0.2 to 1.5 |

* * * * *